(12) United States Patent
Hruschka et al.

(10) Patent No.: US 10,975,244 B2
(45) Date of Patent: Apr. 13, 2021

(54) VALUABLE PRODUCT AND METHOD FOR OBTAINING A VALUABLE MATERIAL PHASE

(71) Applicant: GEA Mechanical Equipment GmbH, Oelde (DE)

(72) Inventors: Steffen Hruschka, Oelde (DE); Wladislawa Boszulak, Oelde (DE); Daniel Michael Martel, Leingarten (DE)

(73) Assignee: GEA Mechanical Equipment GmbH, Oelde (DE)

( * ) Notice: Subject to any disclaimer, the term of this patent is extended or adjusted under 35 U.S.C. 154(b) by 0 days.

(21) Appl. No.: 16/328,195

(22) PCT Filed: Aug. 17, 2017

(86) PCT No.: PCT/EP2017/070848
§ 371 (c)(1),
(2) Date: Feb. 25, 2019

(87) PCT Pub. No.: WO2018/036901
PCT Pub. Date: Mar. 1, 2018

(65) Prior Publication Data
US 2019/0194466 A1    Jun. 27, 2019

(30) Foreign Application Priority Data
Aug. 26, 2016   (DE) .................. 10 2016 115 911.5

(51) Int. Cl.
| | | |
|---|---|---|
| *A61K 36/00* | (2006.01) | |
| *C09B 67/54* | (2006.01) | |
| *C12N 9/02* | (2006.01) | |
| *A23K 10/37* | (2016.01) | |
| *A23L 33/105* | (2016.01) | |
| *A23J 1/14* | (2006.01) | |

(52) U.S. Cl.
CPC .......... *C09B 67/0096* (2013.01); *A23K 10/37* (2016.05); *A23L 33/105* (2016.08); *C12N 9/0061* (2013.01); *A23J 1/14* (2013.01); *C12Y 110/03002* (2013.01); *Y02P 60/87* (2015.11)

(58) Field of Classification Search
None
See application file for complete search history.

(56) References Cited

U.S. PATENT DOCUMENTS

| | | | |
|---|---|---|---|
| 5,980,956 | A | 11/1999 | Petersen et al. |
| 6,045,865 | A | 4/2000 | Felby et al. |
| 2002/0007524 | A1 | 1/2002 | Sorensen |
| 2014/0228550 | A1 | 8/2014 | Hruschka et al. |
| 2015/0299612 | A1 | 10/2015 | Clery et al. |

FOREIGN PATENT DOCUMENTS

| | | |
|---|---|---|
| DE | 696 05 042 T2 | 7/2000 |
| DE | 697 09 672 T 2 | 9/2002 |
| DE | 101 32 529 A1 | 1/2003 |
| DE | 10 2011 050 905 A1 | 12/2012 |
| WO | WO 98/03535 A1 | 1/1998 |
| WO | WO 2015/181203 A1 | 12/2015 |

OTHER PUBLICATIONS

Aracri, Application of laccase-natural mediator systems to sisal pulp: an effective approach to biobleaching or functionalizing pulp fibres. Bioresource technology, (Dec. 2009) vol. 100, No. 23, pp. 5911-5916 (Year: 2009).*
Lacki K. et al., "Transformation of 3,5-Dimethoxy-4-hydroxy Cinnamic Acid and its Derivatives using Enzyme from White-Rot Fungus Trametes versicolor: Enzyme Characteristics and its Application", Journal of Chemical Technology and Biotechnology, Mar. 1996, pp. 211-220, vol. 65, No. 3, XP000581224 (10 pages).
Jeroch H. et al. "Chemische Behandlungsverfahren", 1999, pp. 288-289, Eugen Ulmer GmbH & Co., Stuttgart, Germany (two (2) pages).
International Search Report (PCT/ISA/210) issued in PCT Application No. PCT/EP2017/070848 dated Nov. 28, 2017 with English translation (nine (9) pages).
German-language Written Opinion (PCT/ISA/237) issued in PCT Application No. PCT/EP2017/070848 dated Nov. 28, 2017 (eight (8) pages).
German Search Report issued in counterpart German Application No. 10 2016 115 911.5 dated Mar. 24, 2017 with partial English translation (13 pages).
Kunamneni A. et al., "Laccases and Their Applications: A Patent Review", Recent Patents On Biotechnology, Jan. 1, 2008, pp. 1-50, vol. 2, No. 1, XP055422269, Madrid, Spain (50 pages).
Lacki K., et al., "Comparison of Three Methods for the Determination of Sinapic Acid Ester Content in Enzymatically Treated Canola Meals", Applied Microbiology And Biotechnology, May 1, 1996, pp. 530-537, vol. 45, No. 4, XP035171318, Springer-Verlag, Berlin, Germany (eight (8) pages).
Menner et al., "Fractionation of Raw Plant Materials", Chemie Ingenieur Technik, vol. 81, No. 11, pp. 1743-1756, Nov. 2009 (two (2) pages).
Niu Y. et al., "Characterization of the Factors that Influence Sinapine Concentration in Rapeseed Meal during Fermentation", Plos One, pp. 1-12, Jan. 21, 2015, vol. 10, No. 1, XP055423476 (12 pages).
Osma J. et al., "Uses of Laccases in the Food Industry", Enzyme Research, Jan. 1, 2010, pp. 1-8, vol. 2010, XP055422279 (eight (8) pages).
Pardo I. et al., "Re-Designing the Substrate Binding Pocket of Laccase for Enhanced Oxidation of Sinapic Acid", Catalysis Science & Technology, Jan. 1, 2016, pp. 1-11, vol. 6, No. 11, XP055424538, The Royal Society of Chemistry (11 pages).
Xie T. et al., "Structural Insight Into the Oxidation of Sinapic Acid by CotA Laccase", Journal Of Structural Biology, May 1, 2015, pp. 1-7, vol. 190, No. 2, XP055422094, (seven (7) pages).

(Continued)

Primary Examiner — Qiuwen Mi
(74) Attorney, Agent, or Firm — Crowell & Moring LLP

(57) ABSTRACT

The present invention relates to a valuable product in the form of a flavonoid-containing phenol mixture having intense red coloration and to a method for obtaining a valuable-substance phase, more particularly a red-colored phase, from a native substance mixture.

19 Claims, 1 Drawing Sheet

(56) References Cited

OTHER PUBLICATIONS

Zhang Y. et al., "Hydrogen Peroxide-Resistant CotA and YjqC of Bacillus altitudinis Spores Are a Promising Biocatalyst for Catalyzing Reduction of Sinapic Acid and Sinapine in Rapeseed Meal", Plos One, Jun. 30, 2016, pp. 1-20, vol. 11, No. 6, XP055423478 (20 pages).

Lacki K. et al.,"Transformation of 3,5-dimethoxy,4-hydroxy Cinnamic Acid by Polyphenol Oxidase From the Fungus Trametes Versicolor: Product Elucidation Studies", Biotechnology and Bioengineering, Mar. 26, 2000, vol. 57, No. 6, John Wiley & Sons, Inc. (five (5) pages).

Kroll J. et al., "Rapssamenproteine—Struktur, Eigenschaften, Gewinnung und Modifizierung", Deutsche Lebensmittel-Rundschau, 2007, pp. 109-118 with English-language abstract(11 pages).

\* cited by examiner

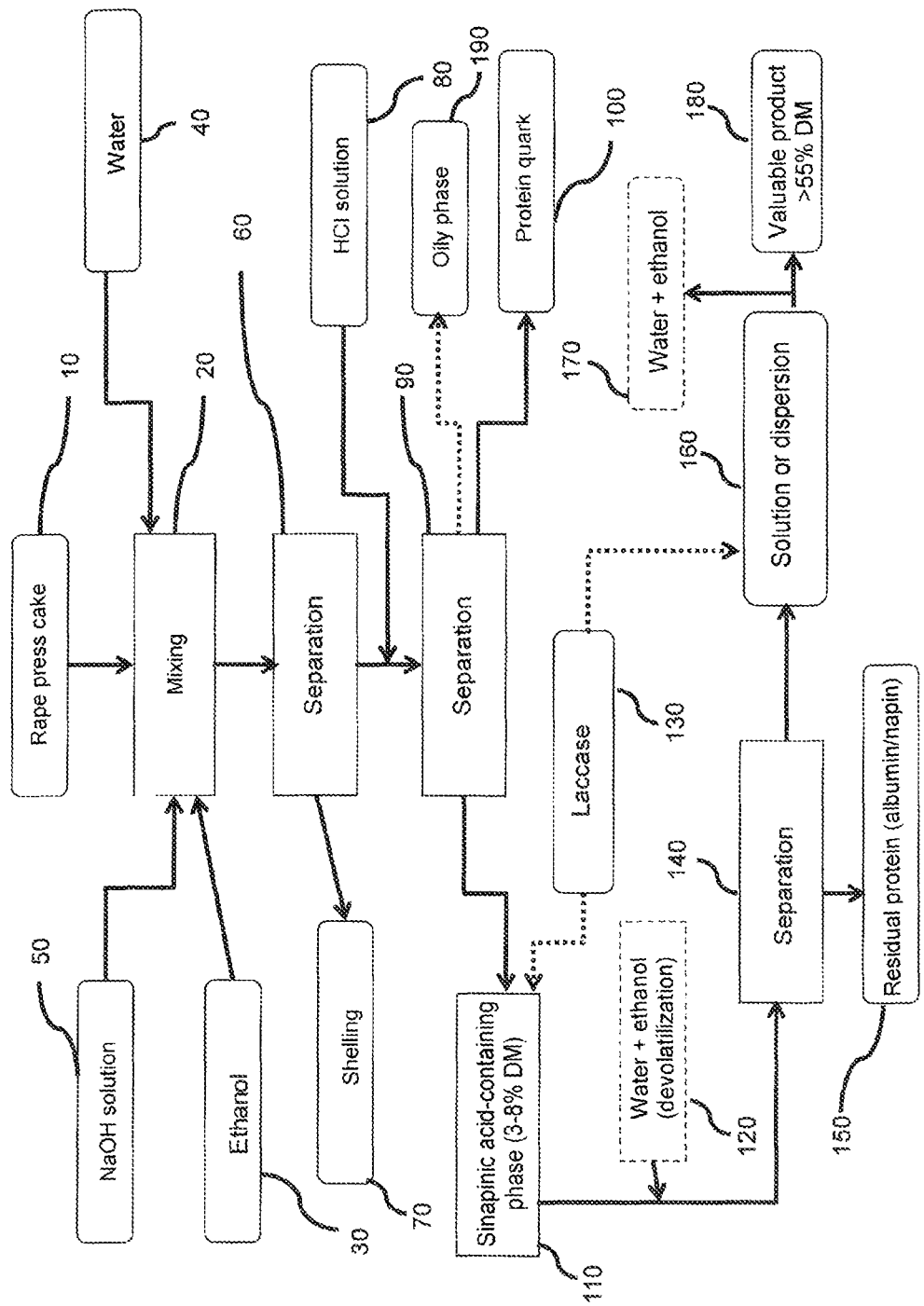

VALUABLE PRODUCT AND METHOD FOR OBTAINING A VALUABLE MATERIAL PHASE

The present invention relates to a valuable product in the form of a flavonoid-containing phenol mixture having intense red coloration and to a method for obtaining a valuable-substance phase, more particularly a red-colored phase, from a native substance mixture.

Obtaining a protein phase as valuable-substance phase from seeds having hard, breakable shells, especially from rape fruits, is known.

The common approach to producing protein concentrates involves washing the coarse meals (greatly deoiled) to deplete the soluble extraction substances. The value of the deoiled intermediate products greatly depends on the concentration of accompanying substances, such as fibers, sugars and secondary plant substances (Menner, M. et al. "*Fraktionierung pflanzlicher Rohstoffe zur simultanen Erzeugung von Lebensmitteln, technischen Rohstoffen and Energieträgern*" [Fractionation of raw plant materials for the simultaneous generation of foodstuffs, raw technical materials and energy carriers], *Chemie Ingenieur Technik*, volume 81, number 11, pages 1743-1756, November 2009). Said accompanying substances also include polyphenols such as sinapine. The polyphenolic acid "sinapinic acid" occurs especially in rapeseeds (where the sinapine content is approx. 640 mg per 100 g of rape). To separate off accompanying substances such as sinapine, large dilutions are selected, proteins are also denatured (temperature, alcohol), cellulose is enzymatically degraded to yield short-chain carbohydrates; these methods are selected in order to be able to extract the substances better.

Against this background, it is an object of the invention to obtain an intensely red-colored valuable product and to further optimize the obtaining of valuable products from the native substance mixture, and it is intended in particular that it be possible to obtain an intensely red-colored valuable-substance phase from the native substance mixture in a relatively simple manner.

The invention achieves this object by providing a valuable product having the features of claim 1 and by means of a method having the features of claim 10.

A valuable product according to the invention is a flavonoid-containing phenol mixture.

Said flavonoid-containing phenol mixture comprises a reaction product. This is preferably a phenolic compound. Particularly preferably, the phenolic compound can be a flavonoid. The reaction product is formed upon the addition of laccase to a sinapinic acid-containing aqueous and/or alcoholic phase. According to the invention, this alcoholic or aqueous phase is produced from plants and/or plant parts, preferably from seeds and/or fruits from the cabbage family (Brassicaceae), more particularly from rape fruits or camelina. The reaction product is formed in the presence of oxygen.

In the context of the present invention, "sinapinic acid-containing" is also understood to mean sinapinic acid derivatives, for example sinapinic acid esters.

The dimerization of sinapinic acid with laccase in the presence of oxygen to form a red dye is known per se. However, it has been shown that, surprisingly, the red coloration when using a sinapinic acid-containing phase obtained from plants and/or plant parts is distinctly more intense compared to the coloration of the laccase/sinapinic acid reaction product. This may possibly be attributable to the presence of further reaction partners in the alcoholic/aqueous phase that are not present in the case of the reaction of the two pure or isolated reaction partners.

Advantageous embodiments of the invention are subject matter of the dependent claims.

The reaction product can advantageously be present in an aqueous and/or alcoholic solution and/or dispersion. The solution and/or dispersion is, in this case, the valuable product. The reaction product is preferably a phenolic compound and particularly preferably a flavonoid.

The valuable product, i.e., the flavonoid-containing phenol mixture, has a dry matter content of more than 55%. Such an elevated dry matter content increases the stability of the solution, meaning that the reaction product decomposes more slowly or not at all.

In the context of the present invention, aqueous solution is also understood to mean a mixture of water and an organic water-soluble solvent. Said organic water-soluble solvent can be an alcohol, more particularly an alcohol having three or fewer carbon atoms, and particularly preferably ethanol.

By contrast, an alcoholic solution consists solely of alcohol, more particularly of an alcohol having three or fewer carbon atoms, and particularly preferably of ethanol.

The sinapinic acid-containing aqueous and/or alcoholic phase as starting material is advantageously produced from cold-pressed seeds and/or fruits.

The pH of the aqueous and/or alcoholic phase is preferably pH=7 or less.

The aqueous and/or alcoholic phase advantageously has a dry matter content before the addition of laccase of less than 3%, preferably less than 1%.

A method according to the invention for obtaining a valuable-substance phase, more particularly an inventive valuable product from a native substance mixture, comprises the following steps:

Step A: Providing the native substance mixture composed of seeds from the cabbage family (Brassicaceae), having a proportion of hard, breakable shells or in shelled form, more particularly rapeseeds as substance mixture composed of the complete seeds or composed of already (partially) deoiled seeds, more particularly as the press cake remaining as oil-extraction residue when pressing out oil especially with a press;

Step B: If the substance mixture from step A has not yet been comminuted: comminuting the substance mixture to break up the shells if necessary;

Step C: Dispersing the comminuted substance mixture from step A) or B) with water, with addition of preferably up to a maximum of 8, particularly preferably up to a maximum of 6 and more particularly up to a maximum of 5 parts water to one part comminuted substance mixture and with stirring of the water and the comminuted substance mixture to yield a flowable slurry or a dispersion;

Step D): Adjusting the pH of the slurry from step C) into an alkaline range of pH>9.5;

Step E): Adding a water-soluble organic solvent, preferably ethanol, more particularly in water-diluted form, to the slurry from step D) following the adjustment of the pH of the slurry in step D; more particularly in such a way that an alcohol concentration of less than 30% is reached in order to detach the shells from the endosperm of the seeds/fruits;

Step F): Separating off a solid phase comprising the overwhelming proportion of any shells still present, preferably in the centrifugal field in a centrifuge;

Step G): Shifting the pH of the solid phase-cleared slurry from step F) into the pH range of from pH=4.5 to pH=7.2; and Step H): Separating the shell-free slurry, the pH of which was shifted into the acidic range in step G), preferably in a centrifuge, more particularly in at least one decanter or one separator, into multiple phases, wherein at least one of said phases is a polyphenol/albumin liquid phase;

Step I): Adding laccase to the polyphenol/albumin liquid phase of step H) directly or after passing through further intermediate steps.

The polyphenol/albumin liquid phase corresponds to the aforementioned sinapinic acid-containing aqueous and/or alcoholic phase, the polyphenol being the sinapinic acid or a sinapinic acid derivative.

The method according to the invention represents obtaining the aforementioned valuable product having intense red coloration in a particularly economical manner.

Advantageous embodiments of the method are subject matter of the dependent claims.

The polyphenol/albumin liquid phase of step I), to which laccase has been added, assumes a red coloration after a reaction time of not more than 30 min.

Laccase is advantageously added in step I) in the presence of oxygen in the following amount to the polyphenol/albumin liquid phase of step H): at least 0.1 g/L, preferably from 0.15 to 0.25 g/L, of laccase based on an enzyme activity of 0.28 kilounits. This involves the formation of the reaction product according to the invention.

The following phase separation can advantageously take place in step H) in one or two steps, preferably in a centrifuge, more particularly in a decanter or separator:
  oily phase comprising a triglyceride content;
  aqueous phase comprising albumin and a sinapinic acid content; and possibly a third phase comprising a further valuable product.

Moreover, the following phase separation can advantageously take place in step H) in one or two steps, preferably in a centrifuge, more particularly in a decanter or separator, into two valuable-substance phases, with at least one aqueous phase comprising an albumin content and a sinapinic acid content and a residual-oil content.

As substance mixture/starting material, it is possible to process a "recently produced intermediate product", i.e., not more than 31 days have elapsed after the preliminary stage.

As substance mixture/starting material, it is possible to process a "fresh intermediate product", i.e., not more than 3 days must have elapsed after the preliminary stage, preferably even only less than 48 hours, more particularly less than 24 hours.

The substance mixture which can be used in step A is cold-pressed material, more particularly a cold-pressed rape press cake which was pressed at a temperature of less than 70° C., particularly preferably of even less than 60° C.

One or more of the separation steps can advantageously be carried out in a 3-phase decanter or in at least two steps in 2-phase decanters.

One or more of the separation steps can advantageously be carried out in a nozzle separator.

The water-soluble organic solvent can advantageously be a linear aliphatic alcohol.

The content of water-soluble organic solvent in the aqueous part of the slurry (I) after the addition of the water-soluble organic solvent can advantageously be less than 45% by volume, preferably less than 30% by volume and particularly preferably less than 15% by volume.

The temperature can advantageously be below 60° C. over all the method steps, these not including the pressing to generate the press cake.

The temperature can advantageously be below 50° C. over all the method steps, these not including the pressing to generate a press cake as starting material that precedes the method.

Particularly preferably, no further enzymes apart from the laccase or no other chemicals (except for pH adjustment) are added in steps A) to I) and in the entire production method.

The invention further provides a product produced by means of the method according to the invention.

The subject matter of the invention will be more particularly elucidated below on the basis of an exemplary embodiment and with reference to the accompanying FIGURE, where:

FIG. 1 shows a flowchart of an exemplary embodiment for carrying out a method according to the invention for producing a valuable product according to the invention.

FIG. 1 depicts schematically an exemplary workflow for the obtaining of a valuable product having intense red coloration. Said red coloration is well preserved even over a relatively long period during storage under room temperature.

The addition of the laccase 130 can preferably be done at one of both two points. The two options are indicated by dotted arrows.

The method according to the invention preferably comprises the following steps:

Step A)

What is provided as starting material is a native substance mixture composed of seeds having hard, breakable shells, more particularly composed of
  seeds/fruits from the cabbage family (Brassicaceae), more particularly from rape fruits or camelina such as, for example, gold-of-pleasure.

The substance mixture in the context of this application can consist of the complete, but broken seeds. They can be unshelled or partially shelled or completely shelled.

Alternatively, the substance mixture can, however, also consist of an already deoiled product, more particularly of an "intermediate product", i.e., of a press cake 10 remaining after a "preliminary stage", for example the pressing-out of oil especially with a press (e.g., a screw press), as oil-extraction residue.

Particularly preferably, "recently obtained intermediate product" is processed as the starting material, i.e., not more than 31 days must have elapsed after the preliminary stage.

The seed can be freshly harvested or else days, weeks or months old; the intermediate stage (the pressing) should take place just before or even immediately before the further processing, so that the material—the seed—has not changed excessively after the oil extraction.

Very preferably, "fresh material" is processed as the starting material, i.e., not more than 3 days must have elapsed after a preliminary stage or preliminary processing (oil extraction), preferably even only less than 48 hours or 24 hours or 12 h or less than 1 h.

With respect to the yield and the purity of the valuable products, good results are achieved using material from a period just after the preliminary stage or/and generally even better results are achieved using fresh material.

The press cake 10 can have a residual-oil content which can even be 20% or greater. Despite high residual-oil contents of this kind, obtaining a protein phase as well is easily realizable with the invention. However, in this connection, obtaining protein is merely optional. The sinapinic acid and/or the sinapine salt as possible sinapinic acid derivative can thus be obtained as sole valuable product of the substance mixture or be obtained as additional valuable product when obtaining protein.

Step B)

If it is still not comminuted: comminution of the substance mixture from step a) to break up the shells. If a press cake is used, it is broken up while still warm, ideally immediately after the pressing. This generates a comminuted material—a kind of granular material—from the press cake. The substance mixture (partially) deoiled beforehand by means of a pressing operation is generally only comminuted, for example crumbled or granulated, or the shells are broken up in any case.

Step C)

The provided and comminuted substance mixture from step A) or B) is dispersed by mixing 20 with water 40 and/or an aqueous solution (e.g., a salt solution). Preferably up to a maximum of 8, preferably up to a maximum of 5 parts (proportions by weight) water are added to one part "comminuted product". Water and comminuted product are then stirred, yielding a flowable slurry or a dispersion. The stirring is done preferably for more than 30 min, more particularly for more than 1 h.

Step D)

What is done next is an adjustment of the pH of the slurry (I) from step c) into an alkaline range; preferably, the pH of the slurry or of the dispersion is adjusted to pH 10 to 11 using alkaline solution 50. At the same time, the stirring is (carefully) continued. The stirring time is preferably more than 30 min; preferably, it is 1 h or above.

Step E)

In this further step, what is done is an addition of at least one water-soluble organic solvent, preferably of alcohol 30, more particularly in water-diluted form, following the adjustment of the pH of the slurry in step D. Preferably, the alcohol ethanol or EtOH (preferably 30-60% by volume) is used to bring the dispersion, the pH of which was adjusted into the alkaline range, to an alcohol concentration of 20-15% by volume or less, more particularly 12% EtOH concentration. It is possible, in line with the amount of water in the alcohol used, to reduce the amount of water in step C by the water present in the alcohol, more particularly in the 30-60% EtOH. The shells thereby detach from the endosperm (cotyledon) with the residual oil and can be separated off, more particularly by means of centrifugation.

As a less preferred alternative in relation to ethanol, it is also possible to use other alcohols, for example isopropanol.

Steps C-E can be carried out together, for example simultaneously. For example, it is possible to adjust an aqueous highly diluted ethanol solution with alkaline solution to an appropriately basic pH and to add this solution to the comminuted substance mixture.

Step F)

In step F), what therefore takes place in a first separation 60 is that a solid phase comprising the overwhelming proportion, preferably more than 80% by weight, of the shells 70 is separated off from the slurry, preferably in the centrifugal field in a centrifuge, or what takes place is that the slurry is cleared of shell solids, especially in a decanter.

In said step, the shells are separated from the rest of the slurry using a decanter with an infeed.

The lighter phase of a centrifugal phase separation is hereinafter also sometimes referred to as upper layer, and the solid phase as heavy phase. A middle phase would accordingly be therebetween with regard to its density.

Step G)

The slurry from step F) which is shell-free to the greatest possible extent in any case is then further processed. What is preferably done in this connection is a precipitation of the dissolved protein content from the shell-free slurry, which, together with the undissolved or partly dissolved protein portion, forms a fraction, the quark. In this connection, the pH is shifted further again into the acidic range, more particularly into the pH range of from pH=4.5 to pH=7. To this end, hydrochloric acid 80, preferably in diluted form, can be added.

Step H)

Then, the shell-free slurry, the pH of which was shifted again into the acidic range, is separated by means of a second separation 90—preferably in a centrifuge, more particularly in at least one decanter or in a separator—in one or two steps into valuable-substance phases, of which one phase is a protein-concentrate phase and one of these phases is a sinapinic acid-containing liquid phase;

Particularly preferably, what takes place is a separation into the following two or three phases:

oily phase 190, which is indicated as optional separate phase by dotted arrows aqueous phase (sinapinic acid-containing) 110 protein-concentrate phase (hereinafter also called "protein quark") 100 or aqueous sinapinic acid-containing phase with residual-oil content 110; and protein-concentrate phase (protein quark) 100;

In the aqueous phase, further dissolved plant components may be present. These are, inter alia, one or more albumins and/or polyphenols and/or further plant components which are present in the abovementioned plants and which were not separated off as solids under the abovementioned conditions.

The two-phase separation is carried out when the raw material is relatively greatly deoiled and/or is present in solid-bound form or when no intense shearing influence has been performed. The addition of water or alcohol or alkaline solution or the like can also be done in substeps. The oil as lighter phase contains triglycerides and is one of the obtainable valuable substances.

Step I) Addition of laccase 130 to the sinapinic acid-containing liquid phase of step H) with or without residual-oil content, directly or after passing through further intermediate steps. The sinapinic acid-containing liquid phase 110 of step I), to which laccase 130 has been added, assumes a red coloration after a reaction time of preferably less than 30 min.

What are mentioned for the most part hereinafter are the sinapinic acid and sinapinic acid-containing phases and substance mixtures. However, it is understood that, depending on the pH, the sinapinic acid can also be present as sinapinic acid derivative, for example esterified with choline. The sinapinic acid can thus also be present as sinapinic acid derivative in the phase in question. These compounds are likewise encompassed by the terms "sinapinic acid" or "sinapinic acid-containing".

Preferably, the temperature over all the method steps is below 60° C., more particularly below 50° C., preferably between 40° C. and 50° C., making it possible to obtain particularly valuable products.

The denaturation of the proteins is a temperature- and time-dependent process. Another factor is the condition in the alcoholic environment. The higher the temperature, the faster the protein denaturation. However, in an aqueous environment, no irreversible protein denaturation can be expected even with heat exposures of 45-50° C. This changes, however, with the concentration of alcohol. At just ambient temperature, it is possible to observe protein precipitation with highly concentrated alcohol.

The lower the alcohol concentration then, the higher the temperature needs to be in order to denature the proteins. Or conversely: the more aqueous the alcohol concentration, the higher the working temperature may be without the proteins being irreversibly damaged.

What will thus be selected (for pure water) is a highest possible temperature, i.e., ideally reaching 60° C., in order to bring as many substances as possible into solution, such as proteins, lecithins, glycolipids, etc. However, care should be taken that the temperature remains sufficiently low in line with the process parameters time and alcohol concentration (optionally pressure).

The precipitated proteins from step H) are present as protein quark (heavy phase). They form a further valuable substance of the obtainable valuable substances. This phase can be thoroughly dried to form powder.

After step I), what is obtained after a sufficient reaction time has passed is a fluid of red coloration which is also optically attractive and therefore easily further utilizable. The fluid has a coloration resembling the color of the "beetroot" fruit. Standardized colors are referred to as RAL colors (RAL GmbH, subsidiary of the RAL Institute). Assigned to each color is a four-digit color number. Theoretically, any press cake can be used for the method.

The advantageous specified temperature in relation to method steps A to H does not concern the pressing temperature when generating the press cake in the generation of oil. The higher the temperature in the preceding process steps, the browner the protein phase or quark fraction. This is due, firstly, to the Maillard reaction of sugars with proteins and, secondly, to the phenol oxidation. Compared to DE 10 2011 050 905 A1, what is obtained, especially through the use of an optimally selected starting material (preferably cold-pressed rape press cake, preferably very fresh), is a product which is particularly attractive and particularly easily further utilizable.

What is particularly advantageous is the use of a cold-pressed material, more particularly a cold-pressed rape press cake (pressing temperature advantageously less than 70° C., particularly preferably even less than 60° C.) as starting material or as the provided substance mixture. A warm-pressed material is exposed, during the pressing, to distinctly higher temperatures (to over 100° C.). Through the use of a cold-pressed material as starting material for the method according to the invention, it is possible to obtain a protein phase or "protein or quark phase" having distinctly better properties (distinctly brighter especially with respect to the color and therefore better processable) and having a distinctly better yield than when using a warm- or hot-pressed starting material. This has hitherto not been recognized in the prior art. This is because common rape pressing methods aim for a high oil yield, and so higher temperatures are readily used for the pressing. What can be stated as the side effect is that sinapine (a polyphenol) is degraded, which would be advantageous per se for the protein fraction. However, in the method according to the invention, the original, i.e., nonreduced, sinapine content in the cold-pressed cake is nevertheless not a problem for the end product, since the polyphenolic compounds are substantially not to be found in the quark phase, since they pass into the water phase.

In the liquid phase or "water phase" of step H), valuable ingredients are additionally present; more particularly, said phase is albumin-containing and/or sinapinic acid-containing to a relatively great extent. In addition, the liquid phase is enriched with sinapine, sinapinic acid and/or sinapinic acid derivatives. In this respect, the obtaining of a red-colored fluid by means of the invention is useful and advantageous.

Following step I), what can take place in a step K) is a devolatilization 120 for the partial removal of water and/or ethanol, preferably at gentle temperatures. This can advantageously be done by means of vacuum or negative pressure. This is particularly advantageous, the higher the ethanol content in the aqueous phase.

Lastly, what can take place in step L) is a residual-protein phase 150 being optionally separated off by means of a third separation 140. The residual-protein phase 150 contains, in particular, albumins and/or napins, which can be separated off as solids by means of a separator, more particularly by means of a decanter. This can optionally be done under the addition of additives, such as, for example, enzymes; complexing agents and/or precipitants, such as, for example, ammonium sulfate The laccase according to step I) can be added either before or after the optional steps K and/or L. In step I), the reaction of the sinapinic acid and/or of the sinapinic acid derivative with the laccase takes place take place particularly preferably in the presence of oxygen. Preferably, it is possible to additionally introduce oxygen, for example by means of air recirculation, during the reaction.

Sinapinic acid or a sinapinic acid derivative and laccase is involved in the reaction. However, what is also additionally possible is the involvement of one or more further substances which are carried along in dissolved form in the aqueous/alcoholic phase during the preceding steps A-H, and preferably also in the optional steps K and L.

The reaction product produced from sinapinic acid, laccase and possibly further reaction products is present in the aqueous/alcoholic solution 160 with a dry matter content of 3-8%.

It has been found that, surprisingly, the red coloration in the case of the addition of laccase to a sinapinic acid-containing phase which arises when processing plants, more particularly Brassicaceae, turns out distinctly more intense than the red coloration which in the case of the reaction of isolated or pure sinapinic acid with laccase arises, as has been described, for example, in the article "Transformation of 3,5-Dimethoxy 4-hydroxy Cinnamic Acid by Polyphenol Oxidase from Fungus Trametes versicolor" (Lacki and Duvnjak, Biotechnology and Bioengineering, Vol. 57, No. 6, pp. 694-703).

In a further step M, what lastly takes place is a stabilization of the reaction product having the intense red coloration. This is achieved by concentration of the reaction product by removal of water and alcohol 170, for example by devolatilization under negative pressure or vacuum. The concentration can take place either as early as in step 120 before the albumins are separated off or only in step 170, or else by a first concentration in step 120 and a second concentration in step 170. What is formed is a red syrup as valuable product 180 having a dry matter content of at least 20 percent, preferably 30-35 percent. However, at the same time, part of the syrup is preferably still water and/or ethanol. Furthermore, the valuable product, i.e., the syrup, can contain residual amounts of sinapinic acid, which residual amounts are, however, below 500 ppm, preferably below 400 ppm. The valuable product is thereby directly usable in the food industry, for example as dye for coloring foodstuffs.

The aforementioned valuable product is preferably a flavonoid-containing phenol mixture. In this connection, the reaction product having the red color is a phenolic compound, more particularly a flavonoid.

In this connection, the majority of the sinapinic acid is preferably converted to form the reaction product upon laccase addition. Thus, the syrup contains less sinapinic acid than reaction product in terms of mol %. Particularly preferably, the amount-of-substance proportion of sinapinic acid can, with respect to the reaction product, be at less than 50%. This means that preferably two thirds of the sinapinic acid have been converted.

Depending on the concentration range and pH, what can occur is a stabilization, a slow decomposition or a rapid decomposition of the dye or the reaction product. Therefore, there are various possible applications for the red reaction product. A solution having a reaction-product concentration of more than 20% can be stored either at a normal ambient temperature of 20-35° C. or at a cool temperature.

The decomposition of the reaction product is, inter alia, pH-dependent. Thus, it is, for example, conceivable to use the reaction product as a color indicator for indicating a cold chain in the food industry, with decomposition of the reaction product occurring in the event of interruption of the cold chain, this being associated with a change in the color of the indicator from intense red to brown.

Moreover, the reaction product can also be used as a stable food coloring, for example for coloring ice cream.

A particularly advantageous method variant shall be elucidated on the basis of the following example.

Step A) In this example, the provided starting material is pressed rape cake, ideally pressed under gentle and cold conditions, having typical residual-oil contents of 20%; even higher is not a problem.

Step B) The cake is broken up, ideally immediately after the pressing, while still warm.

Step C) The granular cake material is dispersed using water (1 part cake and not more than 6 parts water) and must be stirred carefully (1 h).

Step D) This dispersion must be adjusted to pH 10 to 11 using alkaline solution and stirred carefully, usually for 1 h.

Step E) The dispersion from D must be brought to an EtOH concentration of 12% by volume using EtOH (preferably 30-60%-based on percent by volume); the amount of water in point C is thus reduced by the water present in this 30-60% EtOH. Step F) The shells thereby detach from the endosperm (cotyledon) with the residual oil and can be separated off by means of centrifugation. The result is an upper layer and a shell fraction.

Step G) Precipitation of the protein, by acidification to preferably pH=4.5 to 7.2, from the upper layer (upper layer: light phase of the separation from step F) having a pH of preferably from 9.7 to 10.5) for the purposes of separation: oil—aqueous sinapinic acid-containing phase—protein-concentrate phase (protein quark) or separation into sinapinic acid-containing oil/water phase and protein-concentrate phase; this step can be supported by an intense shearing in order to facilitate the release of oil.

Step H) Separating off the precipitated proteins as quark (heavy phase (generally solid phase or, in this case, quark phase)) and possibly triglycerides (as light oil) from the upper layer (light phase or alcoholic/aqueous phase), especially by means of centrifugation.

Step K) Devolatilization of the light alcoholic/aqueous phase

Step L) Optionally separating off a protein residual phase from the sinapinic acid-containing alcoholic/aqueous phase Step I) Addition of laccase to the sinapinic acid-containing alcoholic/aqueous phase after steps H), K) and/or L) with or without residual-oil content and waiting for a reaction time until a red coloration appears.

Step M) Stabilization of the alcoholic/aqueous phase by removal of alcohol or water with adjustment of a dry matter content of greater than 20%, preferably between 30-35%.

For better illustration, the separation shall be elucidated below on the basis of a few examples.

Example

B1) A cold-pressed protein-containing cake which is processed up to step F has, after its processing, the following phases: 17% heavy phase as shell content from the infeed containing 20% of the cake proteins and 83% upper layer as protein/polyphenol/oil/phosphatide phase containing 80% of the cake proteins.

B2) A warm-pressed cake which is processed up to step F has, after its processing, the following phases: 26% heavy phase as shell content from the infeed containing 30% of the cake proteins and 74% upper layer as protein/polyphenol/oil/phosphatide phase containing 70% of the cake proteins.

B3) A hot-pressed cake which is processed in step F has, after its processing, the following phases: 30% heavy phase as shell content from the infeed containing 50% of the cake proteins and 70% upper layer as protein/polyphenol/oil/phosphatide phase containing 50% of the cake proteins.

Regarding step G)—Protein Precipitation

From the upper layer (upper layer=light phase) from the separation in the preceding step, the proteins are precipitated by a pH shift to the range of from 4.5 to approx. 7. The water-insoluble proteins, which are swellable in aqueous solution however, form, together with the precipitated globulins, the "protein quark" protein fraction. The liquid in this fraction has the same composition as the liquid of the middle phase (upper layer without triglycerides). However, since the quark phase accounts for only 10-30% by weight of the infeed (with a relatively high dry matter content, 15-25% by weight of dry matter), substantially fewer polyphenols can also be quantitatively found in the quark phase than in the middle phase, even though the concentration of the polyphenols, based on the water, is the same.

What is thereby available is a protein phase composed of water-insoluble, but swollen proteins with globulins, which protein phase is polyphenol-depleted. This combination composed of an alkaline/ethanolic environment in steps A-F followed by an acidic/alcoholic environment for protein precipitation represent very good conditions for a polyphenol extraction. Surprisingly, the observation, for rape (sinapine and derivatives) here, has been confirmed for other polyphenols (tyrosol and derivatives and others) from other fields such as the processing of olives, even though distinctly more reaction-active substances such as proteins and sugars are present in the suspension.

This means that dilutions, as described in the literature, for achieving equivalent polyphenol aqueous extraction rates are obsolete (for instance, in turn, Kroll et al., "*Rapssamenproteine—Struktur, Eigenschaften, Gewinnung und Modifizierung*" [Rapeseed proteins—structure, properties, extraction and modification], *Deutsche Lebensmittel-Rundschau*, No. 3, 2007, p. 109.

Since the pure triglyceride is displaced from the liquid as light phase, the residual-oil content in the protein end product can be lowered to below 15% by weight, even below 13% by weight, based on dry matter.

Since the temperatures over the entire process are <=50° C., a native end product can also be spoken of.

It is advantageous to shear the slurry to be processed further, before the phase separation of step H (before oil is separated off) and after step F) or G) of claim 1, in order to improve the displacement extraction. Said shearing can be carried out using a shearing device, such as, for example, a homogenizer or an intensive mixer, in order to thereby obtain even more oil.

The shearing using a shearing device can be carried out in a continuous process. Altogether, a continuous process is preferably realized.

In further experiments, it has become apparent that, in the case of a pretreatment of steps C), D) and E), the sinapinic acid is enriched in the "water phase". This is advantageous for the present method. Thus, the choice of starting material has an influence on the amount of the sinapinic acid available for the reaction.

In the individual experiments, different batches composed of differing raw material or starting material plus water were selected; although the samples had different amounts, this was normalized or appropriately converted.

It was found, that the polyphenol content in the aqueous phase can rise to more than 4-fold when the starting material used is "cold-pressed rape press cake" instead of "hot-pressed rape press cake". Using fresh material is also advantageous in this respect. Just as the polyphenol content is enriched in the water phase, it is depleted in the protein quark phase. Thus, in the case of a hot-pressed cake, the proportion of 9.4% polyphenols (dry matter "DM" in the raw material) is depleted to 5.6% by weight DM in the protein quark or quark powder and, in the case of the cold-pressed cake, it is depleted from 18.6% by weight DM to 10.1% by weight DM in the quark powder. Thus, this concentration of the polyphenols, based on the solid dry mass, is only about half that in the starting material.

What is thereby available is a protein phase composed of water-insoluble, but swollen proteins with globulins, which protein phase has been depleted with respect to the polyphenol content. Remaining in the water phase are approx. 55% by weight of the polyphenols in the following concentrations:

| Cake type | Dilution in the method Parts water based on 1 part cake | PP in the water phase (mg) | PP in the water phase normalized to a dilution of 1 part seed + 6 parts fluid |
| --- | --- | --- | --- |
| Cold | 4.5 | 3976 | 2982 |
| Warm | 4.2 | 3183 | 2228 |
| Hot | 6.0 | 1053 | 1058 |

The following influencing factors should be noted when processing: in the case of the hot-pressing, polyphenols (PP) are degraded. What has been measured is that the PP content in the case of a cold-pressed seed was 18 mg/g, but 8.8 mg/g in the case of a hot-pressed seed. Similar values are known from the literature (6.2 mg/g in Jeroch et al. 1999). Besides the reduction of the polyphenols in the raw material, there is a deesterification of the sinapine to form sinapinic acid.

The cold-pressing means that, according to the above-mentioned method, the transfer of the polyphenols into the water phase or, more precisely, "polyphenol/albumin phase" of step H) is quantitatively the greatest in the case of the cold-pressing. As a consequence of the alkaline pretreatment (+temperature and EtOH), they are substantially present as sinapinic acid or salts of the sinapinic acid and no longer as sinapine and not yet as canolol.

It is then advantageous to add an enzyme, more particularly laccase, to the "polyphenol/albumin phase" of step H. The enzyme "Laccase C" from ABA Spezialsysteme GmbH, Wolfenbüttel, Germany, has been found to be particularly advantageous. Said enzyme is preferably added in at least 0.1 g/L, preferably from 0.15 to 0.25 g/L, of laccase based on an enzyme activity of 0.28 kilounits.

Preferably, at least 30% by weight, preferably over 50% by weight, of the dry matter of the valuable product comprises the reaction product formed from laccase and the aforementioned naturally obtained sinapinic acid.

In this connection, a shelled, singly or doubly deoiled rape press cake has been found to be particularly suitable for processing. In the case of a cold-pressed rape press cake, the sum of the sinapine content and the sinapinic acid content is greater than in the case of the warm-pressed rape press cake. Moreover, it is advantageous when the proportion of sinapinic acid in the sinapine/sinapinic acid mixture is as high as possible.

It is advantageous to select the conditions of steps C) to F) such that as much sinapinic acid as possible is formed. To this end, it is advantageous when the pH in step D) is greater than 10, when the residence time t is at least 30 min or more, and when the temperature is at least T=20° C. In the case, too, of steps E) to H), the temperature is advantageously at least 20° C.

Cleaving off a choline group from the sinapine to form sinapinic acid is more efficient in the alkaline environment and at slightly elevated temperatures.

A red fluid is obtained from the upper layer of step H), the polyphenol/albumin phase having a sinapine/sinapinic acid content, a brown fluid containing at least, for example, approx. 8% DM, of this 2% protein (85% of which is in turn water-soluble napin) and approx. 6-7% sugars and some oily substances.

Thereafter, the enzyme laccase is added to the upper layer (preferably at room temperature) in the amount of 0.1 g from a solution containing 10000 units (1 g amount), i.e., approximately 1000 units. This is followed by ventilation for at least 30 min, preferably approx. 1 hour. 1+1 (1 kUnit) are sufficient to bring about a result. After a sufficient reaction time T has passed, the upper layer to which laccase was added becomes red. The result is a red fluid having a coloration in the manner of the colors RAL 3004, 3005 and/or 3006. The resultant color resembles the color of the "beetroot" fruit. The resultant fluid has multiple possible uses, for instance as food additive for coloring in the manner of a color of the type "beetroot".

The valuable product can be a valuable product comprising additionally residual protein (album in/napin) in addition to the reaction product, or it can be a valuable product which has been cleared of said residual protein to the greatest possible extent by means of an additional separation 140.

REFERENCE SIGNS

10 Rape press cake
20 Mixing
30 Ethanol
40 Water
50 Alkaline solution
60 Separation
70 Shelling
80 Hydrochloric acid solution
90 Separation 100 Protein quark
110 Sinapinic acid-containing phase
120 H2O+EtOH removal
130 Laccase
140 Separation
150 Residual protein
160 Solution and/or dispersion
170 H2O+EtOH removal
180 Valuable product (more than 30% DM)

The invention claimed is:

1. A method for obtaining a valuable-substance phase comprising the following steps:
   Step A: providing a native substance mixture composed of seeds and/or fruits from the cabbage family Brassicaceae, having comminuted as a proportion of hard, breakable shells or in shelled form, wherein the native substance mixture is rapeseeds composed of complete seeds or composed of partially deoiled seeds;
   Step B: if the native substance mixture from step A) is not completely comminuted, further comminuting the native substance mixture from step A) to break up the shells;
   Step C: dispersing and/or mixing the comminuted substance mixture from step A) or B) with water, with addition of up to a maximum of 8 parts water to one part comminuted substance mixture and with stirring of the water and the comminuted substance mixture to yield a flowable slurry or a dispersion;
   Step D: adjusting the pH of the slurry from step C) into an alkaline range of pH>9.5;
   Step E: adding a water-soluble organic solvent to the slurry from step D) following the adjustment of the pH of the slurry in step D); in such a way that an alcohol concentration of less than 30% by volume is reached in order to detach the shells from the endosperm of the seeds/fruits;
   Step F: separating off a solid phase comprising the overwhelming proportion of any shells still present, wherein the separation is performed in the centrifugal field in a centrifuge;
   Step G: shifting the pH of the solid phase-cleared slurry from step F) into the pH range of from pH=4.5 to pH=7.2; and
   Step H: separating the shell-free slurry, the pH of which was shifted into the acidic range in step G), wherein the separation is performed in a centrifuge into multiple phases, wherein at least one of said phases is a sinapinic acid-containing phase;
   Step I: adding laccase to the sinapinic acid-containing phase of step H),
   wherein the phase separation is performed in step H) in one or two steps, into two valuable-substance phases, with at least one aqueous phase comprising an albumin content and a sinapinic acid content and a residual-oil content.

2. The method as claimed in claim 1, characterized in that the native substance mixture is processed in the form of a recently produced intermediate product not more than 31 days after a preliminary stage.

3. The method as claimed in claim 1, characterized in that the native substance mixture is processed in the form of a fresh intermediate product not more than 3 days after a preliminary stage.

4. The method as claimed in claim 1, characterized in that the native substance mixture used in step A) is a cold-pressed material, which was pressed at a temperature of less than 70° C.

5. The method as claimed in claim 1, characterized in that one or more of the separation steps in step F) or H) is/are carried out in a 3-phase decanter or in at least two steps in 2-phase decanters.

6. The method as claimed in claim 1, characterized in that one or more of the separation steps in step F) or H) is/are carried out in a nozzle separator.

7. The method as claimed in claim 1, wherein the water-soluble organic solvent is a linear aliphatic alcohol.

8. The method as claimed in claim 1, wherein the content of the water-soluble organic solvent in the aqueous part of the slurry in step E) after the addition of the water-soluble organic solvent is 20% by volume or less.

9. The method as claimed in claim 1, wherein all the method steps are performed at a temperature below 60° C.

10. The method as claimed in claim 1, wherein all the method steps are performed at a temperature below 50° C.

11. A method for obtaining a valuable-substance phase comprising the following steps:
   Step A: providing a native substance mixture composed of seeds and/or fruits from the cabbage family Brassicaceae, having comminuted as a proportion of hard, breakable shells or in shelled form, wherein the native substance mixture is rapeseeds composed of complete seeds or composed of partially deoiled seeds;
   Step B: if the native substance mixture from step A) is not completely comminuted, further comminuting the native substance mixture from step A) to break up the shells;
   Step C: dispersing and/or mixing the comminuted substance mixture from step A) or B) with water, with addition of up to a maximum of 8 parts water to one part comminuted substance mixture and with stirring of the water and the comminuted substance mixture to yield a flowable slurry or a dispersion;
   Step D: adjusting the pH of the slurry from step C) into an alkaline range of pH>9.5;
   Step E: adding a water-soluble organic solvent to the slurry from step D) following the adjustment of the pH of the slurry in step D); in such a way that an alcohol concentration of less than 30% by volume is reached in order to detach the shells from the endosperm of the seeds/fruits;
   Step F: separating off a solid phase comprising the overwhelming proportion of any shells still present, wherein the separation is performed in the centrifugal field in a centrifuge;
   Step G: shifting the pH of the solid phase-cleared slurry from step F) into the pH range of from pH=4.5 to pH=7.2;
   Step H: separating the shell-free slurry, the pH of which was shifted into the acidic range in step G), wherein the separation is performed in a decanter into multiple phases, wherein at least one of said phases is a sinapinic acid-containing phase; and
   Step I: adding laccase to the sinapinic acid-containing phase of step H),
   wherein the phase separation is performed in step H) in one or two steps, into two valuable-substance phases, with at least one aqueous phase comprising an albumin content and a sinapinic acid content and a residual-oil content.

12. The method as claimed in claim 3, wherein the native substance mixture is processed in the form of a fresh intermediate product less than 48 hours after the preliminary stage.

13. The method as claimed in claim 3, wherein the native substance mixture is processed in the form of a fresh intermediate product less than 24 hours after the preliminary stage.

14. The method as claimed in claim 4, wherein the cold pressed material is a cold pressed rape cake.

15. The method as claimed in claim 4, wherein the cold-pressed material was pressed at a temperature of less than 60° C.

16. The method as claimed in claim 1, wherein in step C), the dispersing and/or mixing of the comminuted substance mixture from step A) or B) with water is with the addition of up to a maximum of 6 parts water to one part comminuted substance mixture.

17. The method as claimed in claim 1, wherein in step C), the dispersing and/or mixing of the comminuted substance mixture from step A) or B) with water is with the addition of up to a maximum of 5 parts water to one part comminuted substance mixture.

18. The method as claimed in claim 1, wherein in step E), the water-soluble organic solvent is ethanol and is in water diluted form.

19. The method as claimed in claim 1, wherein the content of the water-soluble organic solvent added to the slurry in step E) is 30 to 60% by volume.

* * * * *